US007011684B2

(12) United States Patent
Eckman

(10) Patent No.: US 7,011,684 B2
(45) Date of Patent: Mar. 14, 2006

(54) INTERVERTEBRAL DISK PROSTHESIS

(75) Inventor: Walter W. Eckman, Tupelo, MS (US)

(73) Assignee: Concept Matrix, LLC, Orlando, FL (US)

( * ) Notice: Subject to any disclaimer, the term of this patent is extended or adjusted under 35 U.S.C. 154(b) by 0 days.

(21) Appl. No.: 10/345,634

(22) Filed: Jan. 16, 2003

(65) Prior Publication Data
US 2003/0135278 A1 Jul. 17, 2003

Related U.S. Application Data

(60) Provisional application No. 60/369,667, filed on Apr. 2, 2002, provisional application No. 60/349,743, filed on Jan. 17, 2002.

(51) Int. Cl.
*A61F 2/44* (2006.01)
(52) U.S. Cl. .................. 623/17.16; 623/17.11
(58) Field of Classification Search ............. 623/17.11, 623/17.12, 17.13, 17.14, 17.15, 17.16
See application file for complete search history.

(56) References Cited

U.S. PATENT DOCUMENTS

| 4,349,921 | A | 9/1982 | Kuntz |
|---|---|---|---|
| 4,936,848 | A | 6/1990 | Bagby |
| 4,961,740 | A | 10/1990 | Ray et al. |
| 5,258,031 | A | 11/1993 | Salib et al. |
| 5,425,773 | A | 6/1995 | Boyd et al. |
| 5,522,899 | A | 6/1996 | Michelson |
| 5,549,679 | A | 8/1996 | Kuslich |
| 5,562,738 | A | 10/1996 | Boyd et al. |
| 5,571,189 | A | 11/1996 | Kuslich |
| D377,095 | S | 12/1996 | Michelson |
| D377,096 | S | 12/1996 | Michelson |
| D377,527 | S | 1/1997 | Michelson |
| 5,593,409 | A | 1/1997 | Michelson |
| 5,609,635 | A | * | 3/1997 | Michelson ............... 623/17.16 |
| 5,645,596 | A | 7/1997 | Kim et al. |
| 5,669,909 | A | 9/1997 | Zdeblick et al. |
| 5,674,296 | A | 10/1997 | Bryan et al. |

(Continued)

FOREIGN PATENT DOCUMENTS

WO   WO 96/40014 A1   12/1996

(Continued)

OTHER PUBLICATIONS

Helmut D. Link et al., "Link SB Charité Artificial Disc: History, Design & Biomechanics", *Spinal Restabilization Procedures*. Edited by D.L. Kaech and J.R. Jinkins, 293-298 (2002), Berlin, Germany.

(Continued)

*Primary Examiner*—Paul B. Prebilic
(74) *Attorney, Agent, or Firm*—Akin Gump Strauss Hauer & Feld, LLP

(57) ABSTRACT

An intervertebral disk prosthesis includes a first part, and the first part has a top, a bottom having an opening, an outer surface, an inner surface and a socket extending into an interior of the first part from the opening and defined by the inner surface. The outer surface proximate the top contacts a concave portion of a first vertebra. The disk prosthesis further includes a second part including a top, a bottom, and an outer surface. The outer surface proximate the bottom contacts a concave portion of a second vertebra, and the outer surface of the second part proximate the top of the second part cooperatively engages the inner surface of the first part thereby allowing at least two-degrees of freedom of movement.

20 Claims, 11 Drawing Sheets

U.S. PATENT DOCUMENTS

| | | | |
|---|---|---|---|
| 5,702,449 A | 12/1997 | McKay | |
| 5,776,199 A | 7/1998 | Michelson | |
| 5,785,710 A | 7/1998 | Michelson | |
| 5,865,846 A * | 2/1999 | Bryan et al. | 128/898 |
| 5,888,223 A * | 3/1999 | Bray, Jr. | 623/17.16 |
| 5,888,226 A | 3/1999 | Rogozinski | |
| 5,984,967 A | 11/1999 | Zdeblick et al. | |
| 6,039,762 A | 3/2000 | McKay | |
| D425,989 S | 5/2000 | Michelson | |
| 6,113,637 A | 9/2000 | Gill et al. | |
| 6,136,031 A | 10/2000 | Middleton | |
| 6,174,334 B1 | 1/2001 | Suddaby | |
| 6,270,528 B1 | 8/2001 | McKay | |
| 6,419,705 B1 | 7/2002 | Erickson | |
| 6,425,920 B1 | 7/2002 | Hamada | |
| 6,447,547 B1 | 9/2002 | Michelson | |
| 6,454,805 B1 | 9/2002 | Baccelli et al. | |
| 6,468,311 B1 | 10/2002 | Boyd et al. | |
| 6,478,823 B1 | 11/2002 | Michelson | |
| 6,863,689 B1 * | 3/2005 | Ralph et al. | 623/17.16 |
| 2002/0035400 A1 * | 3/2002 | Bryan et al. | 623/17.15 |
| 2004/0034422 A1 * | 2/2004 | Errico et al. | 623/17.11 |

FOREIGN PATENT DOCUMENTS

| | | |
|---|---|---|
| WO | WO 97/14377 A1 | 4/1997 |
| WO | WO 99/332054 A1 | 7/1999 |

OTHER PUBLICATIONS

Paul C. Mcafee, "Artificial Disc Prosthesis: The Link SB Charité III™", *Spinal Restabilization Procedures*, edited by D.L. Kaech and J.R. Jinkins, 299-301 (2002),Towson, MD.

"Prodisc" Brochure, *Spine Solutions, New York, NY*.

"Link SB Charité™ Artificial Disc" Brochure, Maintaining Natural Mobility, Link Spine Group, Branford, Connecticut.

"Prodisc" Brochure, *Spine Solutions: The Non-Fusion Technology Company*.

Spine Arthroplasty, Spine Industry Analysis Series, *Viscogliosi Bros., LLC*, Nov. 2001.

Depraetere, P., et al., Interbody cages in PLIF Surgery: A Multicentric Report, *Journal of Musculoskeletal Research*, vol. 2, No. 1 (1998) 9-14.

* cited by examiner

INTERVERTEBRAL DISK PROSTHESIS

CROSS-REFERENCES TO RELATED APPLICATIONS

This application claims the benefit of U.S. Provisional Application No. 60/369,667 filed Apr. 2, 2002 entitled "DISK PROSTHESIS" and U.S. Provisional Application No. 60/349,743 filed Jan. 17, 2002 entitled "DISK PROSTHESIS," the entire contents of which are incorporated by reference herein.

BACKGROUND OF THE INVENTION

The present invention relates to an apparatus for intervertebral disk replacement and more particularly to an intervertebral disk prosthesis capable of being implanted in a patient utilizing minimally invasive surgical techniques.

Referring to prior art FIGS. 9 and 10, the spine 120, also known as the vertebral column or the spinal column, is a flexible column of vertebrae 100 (special types of bones) held together by muscles, ligaments and tendons. The spine 120 extends from the cranium (not shown) to the coccyx 126, encasing a spinal cord 128 and forming the supporting axis of the body (not shown). The spinal cord 128 is a thick bundle of nerve tissue (nerves) that branch off to various areas of the body for the purposes of motor control, sensation, and the like. The spine 120 includes seven cervical vertebrae (not shown), twelve thoracic vertebrae (not shown), five lumbar vertebrae, $L^I$–$L^V$, five sacral vertebrae, $S^I$–$S^V$, and three coccyx vertebrae 126. The sacral and coccyx vertebrae are each fused, thereby functioning as a single unit. FIG. 10 shows the lumbar region 122, the sacral region 124 and the coccyx 126 of the spine 120 and that the vertebrae 100 are stacked one upon another. The top portion 100a and bottom portion 100b of each vertebrae 100 is slightly concave. The opposing concave vertebral surfaces form the intervertebral space 121 in which an intervertebral disk (not shown) resides. Each of the intervertebral disks has a soft core referred to as a nucleus pulposus or nucleus (not shown).

In FIG. 9, directional arrow 101a is pointing in the posterior direction and directional arrow 101b is pointing in the anterior direction. FIG. 9 shows that each vertebrae 100 includes a body 106 in the innermost portion, a spinal canal 108 and a spinous process 102 at the posterior-most end of the vertebra 100. The vertebrae 100 are substantially similar in composition, but vary in size from the larger lumbar vertebrae to the smallest coccyx vertebrae 126. Each vertebrae 100 further includes two transverse processes 104 located on either side and a protective plate-like structure referred to as a lamina 10. Nerves from the spinal cord 128 pass through the spinal canal 108 and foramina 111 to reach their respective destinations within the body.

The natural aging process can cause a deterioration of the intervertebral disks, and therefore, their intrinsic support strength and stability is diminished. Sudden movements may cause a disk to rupture or herniate. A herniation of the disk is primarily a problem when the nucleus pulposus protrudes, bulges or ruptures into the spinal canal 108 placing pressure on nerves which in turn causes spasms, tingling, numbness, and/or pain in one or more parts of the body, depending on the nerves involved. Further deterioration of the disk can cause the damaged disk to lose height and as bone spurs develop on the vertebrae 100, result in a narrowing of the spinal canal 108 and foramen 111 (not shown clearly), and thereby causes pressure on the nerves emanating from the spinal cord 128.

Presently, there are several techniques, in addition to non-surgical treatments, for relieving the symptoms related to intervertebral disk deterioration. Surgical options include chemonucleolysis, laminectomy, diskectomy, microdiskectomy, and spinal fusion.

Chemonucleolysis is the injection of an enzyme, such as chymopapain, into the disk to dissolve the protruding nucleus pulposus. The enzyme is a protein-digesting enzyme and is used to dissolve the disk material. Since the enzyme is essentially a tissue-dissolving agent, it is indiscriminate in the protein-based matter it dissolves. Should the enzyme be injected into the wrong place, or if there is a breach in the disk capsule that would allow the solution to enter the spinal canal or to contact nerve tissue or the like, the resultant damage to nerve tissue could not be reversed. Even worse, about half of the patients who receive chemonucleolysis treatments experience increased back pain and muscle spasms immediately after the injection and more than half have incapacitating back pain for durations up to three months after such treatments.

A laminectomy is performed to decompress the spinal canal 108 by open surgical techniques under general anesthesia. In this procedure, the lamina 110, (the bone that curves around and covers the spinal canal 108 as shown in FIG. 9), and any disk tissue causing pressure on a nerve or the spinal canal 108, are partially removed. This technique is highly invasive and traumatic to the body, and therefore requires an extended recovery time of about five weeks and a hospital stay of a few days. In addition to the trauma inflicted on the body from even a successful surgery, there are increased risks of future problems due to the removed portion of the lamina 110 which is no longer in place to support and protect the spinal canal 108 at the area where the surgery took place. Further, the vertebrae 100 may shift due to the lack of support in the structure. Thus, simply removing the disk and parts of the vertebral bone is a short-term, pain-relieving corrective action but not a long-term solution.

Diskectomy is a form of spinal surgery wherein part of an intervertebral disk is excised typically through open surgical techniques. Recently, less invasive techniques referred to as percutaneous diskectomy or microdiskectomy have been developed to reduce the surgical trauma to the patient. In microdiskectomy, a much smaller incision is made than in normal open surgeries. A small retractor, working channel or tube is inserted through the posterior muscles (not shown) to allow access to the intervertebral space of a damaged or herniated disk. Surgeons utilize special surgical instruments modified to work in such small openings such as curettes, osteotomes, reamers, probes, retractors, forceps, and the like to cut and remove part of the disk while monitoring their technique using a microscope, a fluoroscope (real-time X-ray monitoring), and/or an endoscope (a miniature TV camera with associated viewing monitor). While this technique is much less invasive than conventional open surgeries, due to their design the instruments presently available tend to extend the length of time of the surgery and may cause possible damage to areas other than the herniated disk.

The removal of a significant amount of disk material or numerous surgeries often increases the instability of the spine 120 thereby necessitating spinal fusion surgery. In a fusion procedure, a damaged disk may be completely removed. Parts of a bone from another part of the body, such as the pelvis, are harvested, and the bone parts or grafts are subsequently placed between the adjacent vertebrae 100 so that the adjacent vertebrae 100 grow together in a solid mass. In the fusion surgery, which is presently performed as an open surgical technique, the posterior lamina 110 and the centers of the vertebral bodies 106 may both be cut. The surgery often involves consequential damage to the associated posterior ligaments, muscles and joints in addition to the removal of part or all of the lamina 110. The recovery time for a normal spinal fusion surgery is significant due not only to the fact that normal movement cannot be allowed until detectable bone growth has occurred between the bone grafts and the adjacent vertebrae 100, but the associated ligaments, muscles and the location where the bone grafts were harvested must also recover. Oftentimes portions of the spine 120 must be immobilized during the recovery period causing added discomfort and inconvenience to the patient.

A relatively new concept (within the past two decades) is intervertebral total disk replacement or nucleus pulposus (nuclear) replacement. Nuclear replacements are generally designed with either a water retaining chemical in a compartment (bag-like container) or with various woven fiber or pad configurations using synthetic materials as a support cushion. In concept, nuclear replacements have significant potential because the annulus and the endplates are substantially preserved, so long as they were not damaged by previous trauma. However, to date, the available nuclear replacements lack the strength of a human disk nucleus pulposus matter and/or the damage to the annulus during implantation may allow extrusion of the nuclear replacement not unlike a disk herniation.

The prior art devices for total disk replacements are generally made with opposing metal bodies and an interstitial polyethylene plastic body or the like. The greatest difficulty to date has been designing a mechanical structure that closely matches that of the human intervertebral disk with regard to such properties as compression, flexion, extension, torsion and the like, not to mention in endurance/durability. Further, prior art intervertebral disk implants are typically as large as a human intervertebral disk so as to match the vertebrae 100 thereby distributing the compressive loads over a greater area, but necessitating extensive open surgery. Even worse, critical support materials, such as the ligaments and endplate 110, are usually cut away during the surgical procedure leaving the newly implanted disk replacement with less stability.

What is required, but not presently provided by the prior art devices and methods, is a device for replacing damaged, failed, and/or removed intervertebral disks that is able to be implanted in a minimally invasive procedure, is easy to use, safe to insert into the body during surgery, and which allows a range of motion in adjacent vertebrae similar to that of the human intervertebral disk. What is further required is an artificial disk or disk prosthesis that allows for rapid patient recovery times and that can be used on an outpatient basis.

BRIEF SUMMARY OF THE INVENTION

Briefly stated, the present invention comprises an intervertebral disk prosthesis. The disk prosthesis includes a first part having a top, a bottom having an opening, an outer surface, an inner surface and a socket extending into an interior of the first part from the opening and defined by the inner surface. The outer surface proximate the top contacts a concave portion of a first vertebra. The disk prosthesis further includes a second part including a top, a bottom, and an outer surface. The outer surface proximate the bottom contacts a concave portion of a second vertebra, and the outer surface of the second part proximate the top of the second part cooperitively engages the inner surface of the first part thereby allowing at least two-degrees of freedom of movement.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
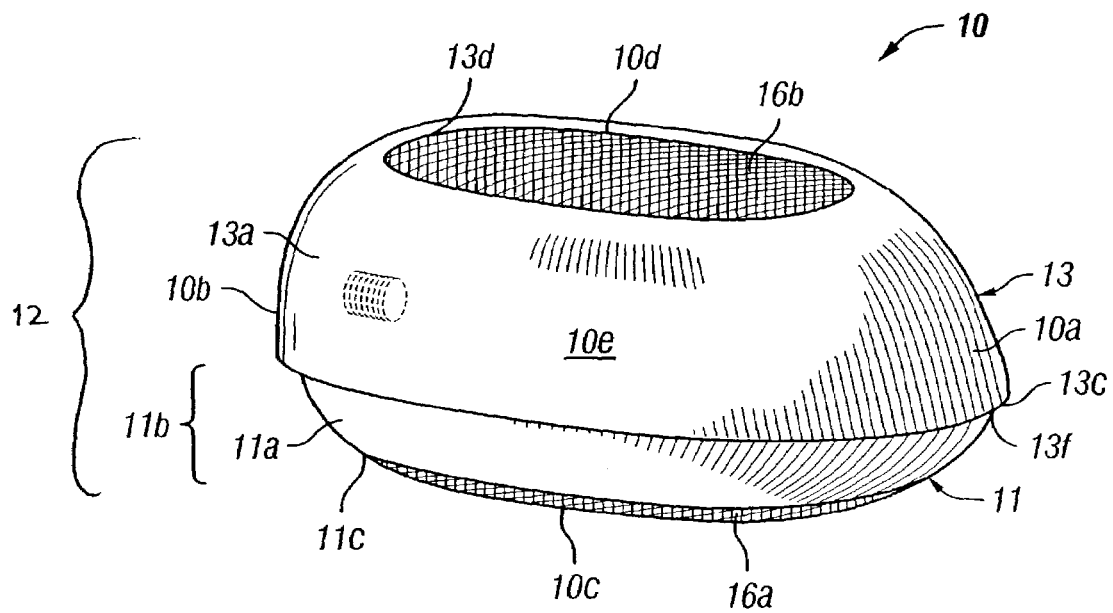
FIG. 1 is a perspective view of a disk prosthesis in accordance with a first preferred embodiment of the present invention.
Figure 2:
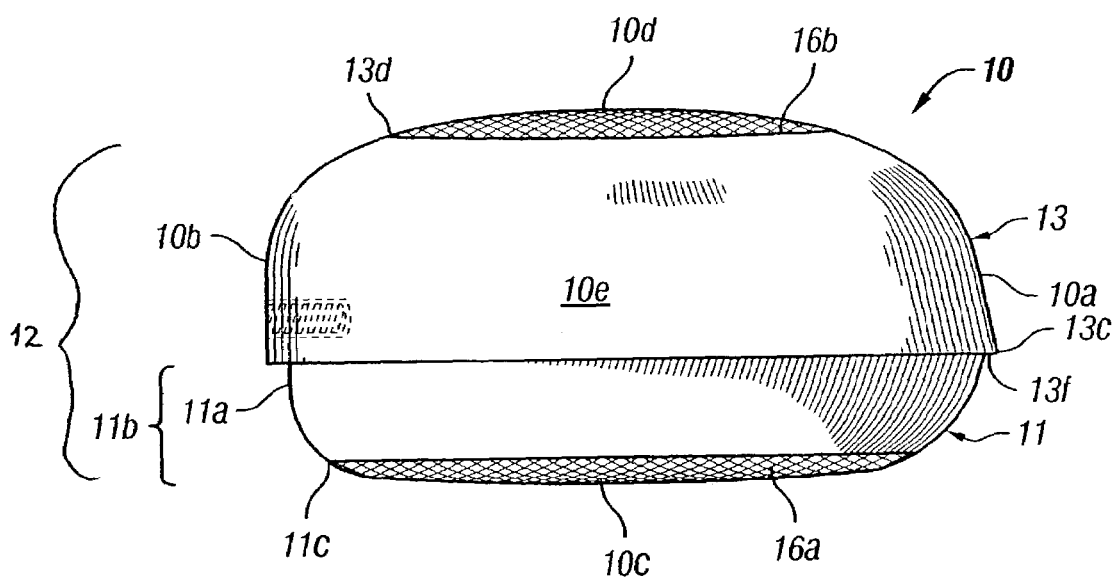
FIG. 2 is a side elevational view of the disk prosthesis of FIG. 1.

Certain terminology is used in the following description for convenience only and is not limiting. The words "right", "left", "lower", and "upper" designate directions in the drawing to which reference is made. The words "inwardly" and "outwardly" refer direction toward and away from, respectively, the geometric center of the disk prosthesis and designated parts thereof. The terminology includes the words above specifically mentioned, derivatives thereof and words of similar import. Additionally, the word "a", as used in the claims and in the corresponding portions of the specification, means "at least one."

Figure 3:
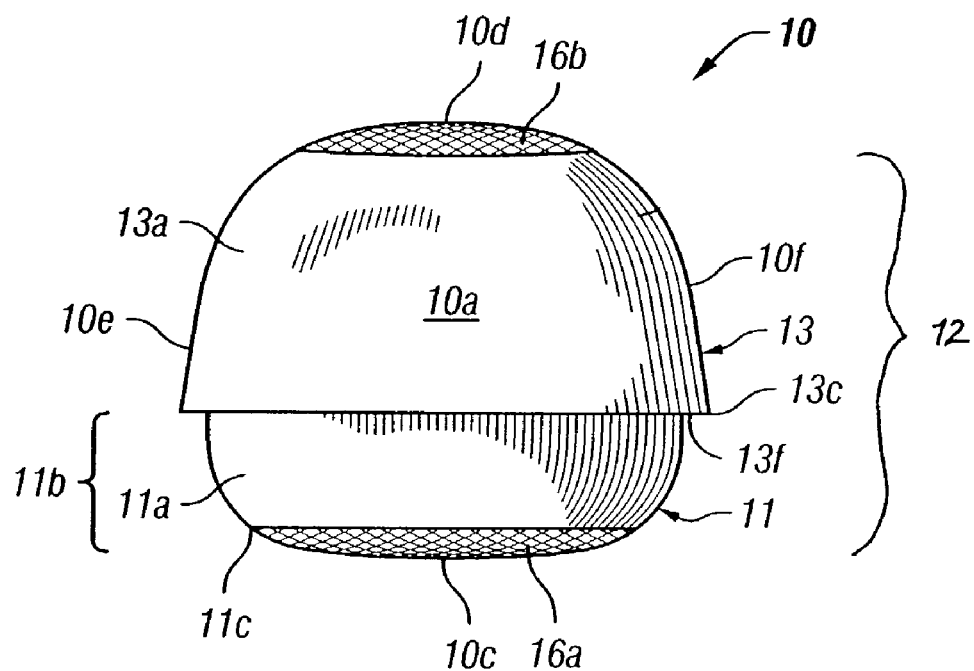
FIG. 3 is a front elevational view of the disk prosthesis of FIG. 1.
Figure 4:
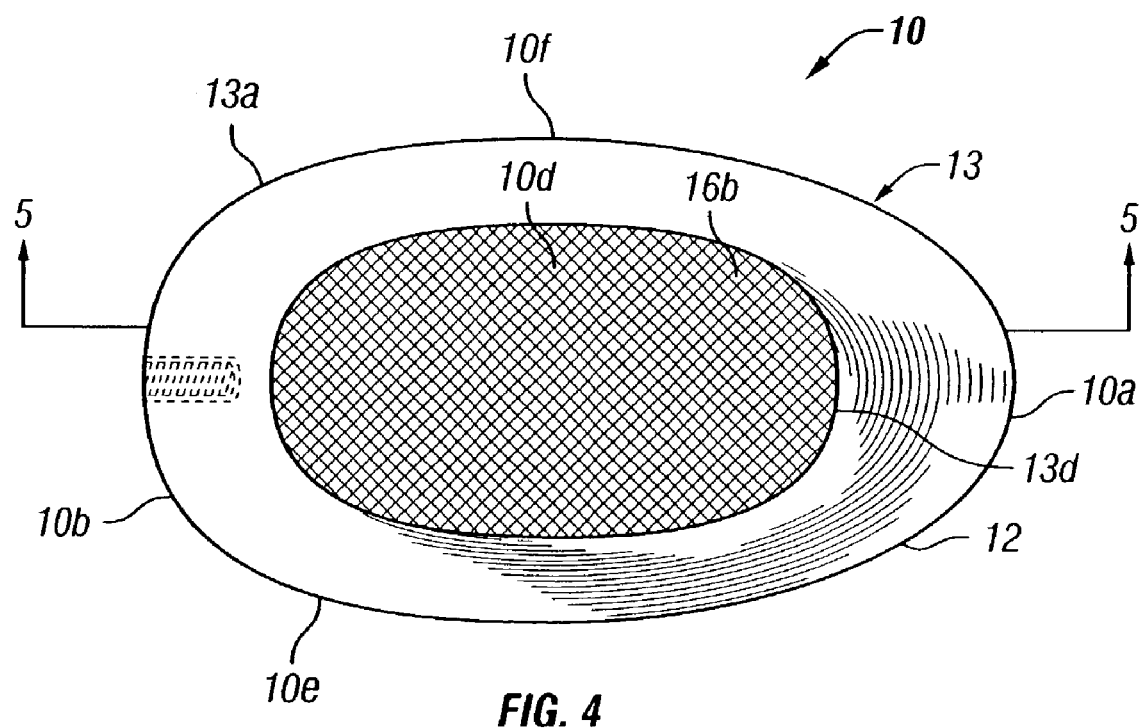
FIG. 4 is a top plan view of the disk prosthesis of FIG. 1.

Referring to the drawings in detail, wherein like reference numerals indicate like elements throughout, there is shown in FIG. 1 an artificial disk or disk prosthesis 10 having a distal end 10a, a proximal end 10b, a lower wall 10c, an upper wall 10d, a first sidewall 10e and a second sidewall 10f (FIGS. 3, 4). The disk prosthesis 10 includes a first part or a cap 13. The cap 13 includes a top 13d, a bottom 13c having an opening 13f, an outer surface 13a, and with reference to FIG. 5, an inner surface 13b and a socket 13e extending into an interior of the cap 13 from the opening 13f and defined by the inner surface 13b. The outer surface 13a proximate the top 13d contacts a concave portion 100b of a first vertebra 100. The disk prosthesis 10 further includes a second part or a base 11 including a top 11d, a bottom 11c, and an outer surface 11a. The outer surface 11a proximate the bottom 11c contacts a concave portion 100a of a a second vertebra 100, and the outer surface of the base 11 proximate the top 11d of the base 11 cooperatively engages the inner surface 13b of the cap 13 thereby preferably allowing at least two-degrees of freedom of movement.

Figure 8:
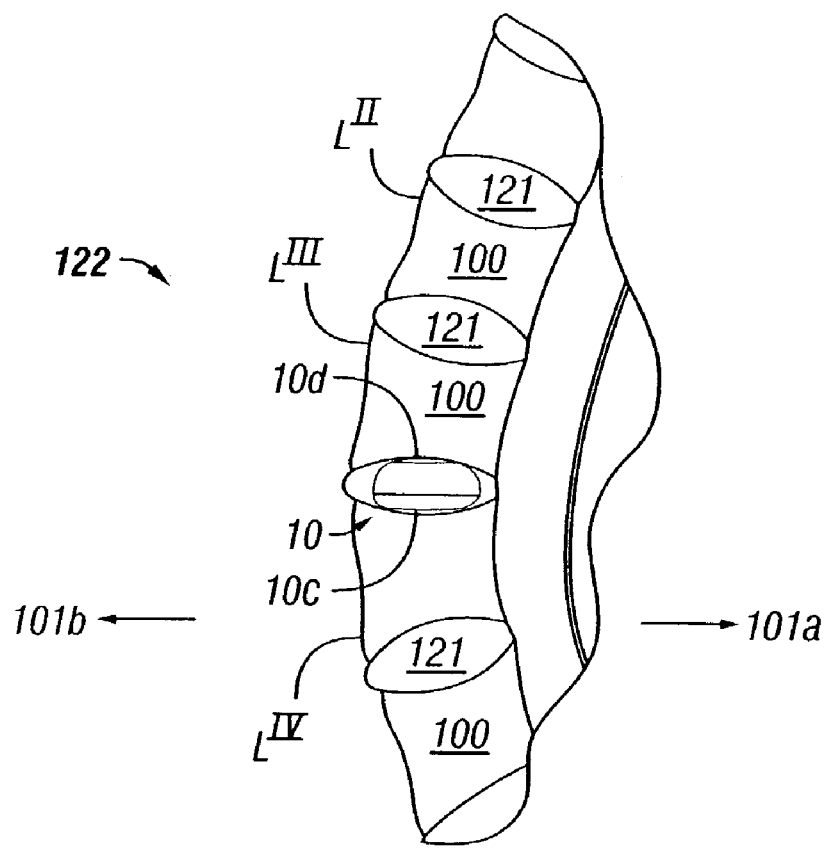
FIG. 8 is a side view of the lumbar section of a human spine with a disk prosthesis shown not to scale installed between vertebra $L^{III}$ and vertebra $L^{IV}$.

As shown in FIG. 8, when inserted into an intervertebral space 121 the cap 13 and the base 11 function together as one overall device, i.e., the disk prosthesis 10. However, it should be noted that the cap 13 and the base 11 are preferably not mechanically connected. In alternate embodiments the cap 13 and the base 11 are connected by a flexible structure or element (not shown) or are totally encased in a pliable, bio-compatible slip-cover or pouch (not shown). The inner surface 13b and a portion 11e of the outer surface 11a that contacts the inner surface 13b are preferably formed of or coated with a bio-compatible, smooth, low-friction material with high durability, such as ceramic, an alloy or the like.

Together, the outer surface 13a of the cap 13 and a portion 11b of the outer surface 11a of the base 11 that is not covered by the cap 13 comprise an outer prosthesis surface 12 that is substantially smooth over the entire surface. The structure of the prosthesis 10 is preferably a bio-compatible metal, a bio-compatible alloy or a bio-compatible ceramic. However, the structure may be titanium, stainless steel, alloys such as a cobalt-chrome molybdenum alloy, polymeric materials, composites, and the like without departing from the broad inventive scope of the present invention.

The disk prosthesis 10 preferably is generally ovoid or egg-shaped and symmetrical along the longer axis with rounded or contoured edges on all sides. The lower wall 10c and upper wall 10d preferably are generally convex in order to cooperatively mate with the natural concavity of adjacent vertebrae 100. Similarly, the first sidewall 10e and second sidewall 10f of the disk prosthesis 10 preferably are similarly convex for similar reasons and to facilitate installation of the disk prosthesis 10 into an intervertebral space 121. The overall shape of the disk prosthesis is such that it can be inserted into an intervertebral space 121 using minimally invasive techniques through a special portal or channel allowing disk arthroplasty on an outpatient basis. In an alternate embodiment of the first preferred embodiment, the proximal end 10b is rounded but more bluntly-shaped than the distal end 10a which is sloped into a bullet-shaped tip.

The lower wall 10c preferably includes a lower mesh structure 16a and the upper wall 10d of the disk prosthesis 10 preferably includes an upper mesh structure 16b at the point of vertebral contact to encourage successful vertebral bone ingrowth thereby affixing the cap 13 to a first or upper vertebra 100 and the base 11 to a second or lower vertebra 100 in an adjacent pair of vertebrae 100. The lower mesh structure 16a and the upper mesh structure 16b may be a grid, a lattice, a plurality of perforations or apertures that extend partially through or completely through the outer surface 12, or any other configuration capable of allowing vertebral bone ingrowth. The mesh structures 16a, 16b may or may not be symmetrically-shaped. The mesh structures 16a, 16b are preferably identically-shaped with respect to one another and are preferably symmetrically-shaped, but need not be. It is contemplated that the mesh structures 16a, 16b are each a larger aperture, or alternatively, are each a generally continuous section of a bio-compatible porous material such as hydroxyapatite coated metals or an irregular metal surface coated with hydroxyapatite coating. It is further contemplated that the mesh structures 16a, 16b are not flush with the edges of the outer surface 12, but are instead slightly below the edges of the outer surface 12 to allow for subsidence of the vertebrae and greater bone ingrowth.

The length of the disk prosthesis as measured from the distal end 10a to the proximal end 10b is approximately 10–30 mm, depending on the particular intervertebral space 121 in which the disk prosthesis 10 is to be inserted. For example, the intervertebral space between lumbar vertebra $L^{III}$ and lumbar vertebra $L^{IV}$ for an average male would accommodate a disk prosthesis 10 of a length between approximately 25–30 mm. But, the length of the disk prosthesis 10 could vary from the aforementioned range without departing from the spirit of the invention.

The width of the disk prosthesis 10 as measured between the first sidewall 10e and the second sidewall 10f of the disk prosthesis 10 will vary from approximately 10 mm to 25 mm depending upon the particular intervertebral space 121 in which the disk prosthesis 10 is to be inserted. For example, the intervertebral space between vertebra $L^{III}$ and vertebra $L^{IV}$ in an average male would accommodate a disk prosthesis 10 having a width of approximately 15–20 mm. But, the width of the disk prosthesis 10 could vary from the aforementioned range without departing from the spirit of the invention.

The height of the disk prosthesis 10 as measured between the upper wall 10d and the lower wall 10c of the disk prosthesis 10 will vary from approximately 5 mm to 25 mm depending upon the particular intervertebral space 121 in which the disk prosthesis 10 is to be inserted. For example, the intervertebral space between vertebra $L^{III}$ and vertebra $L^{IV}$ in an average male would accommodate a disk prosthesis 10 having a height of approximately 8–16 mm. But, the height of the disk prosthesis 10 could vary from the aforementioned range without departing from the spirit of the invention.

Figure 5:
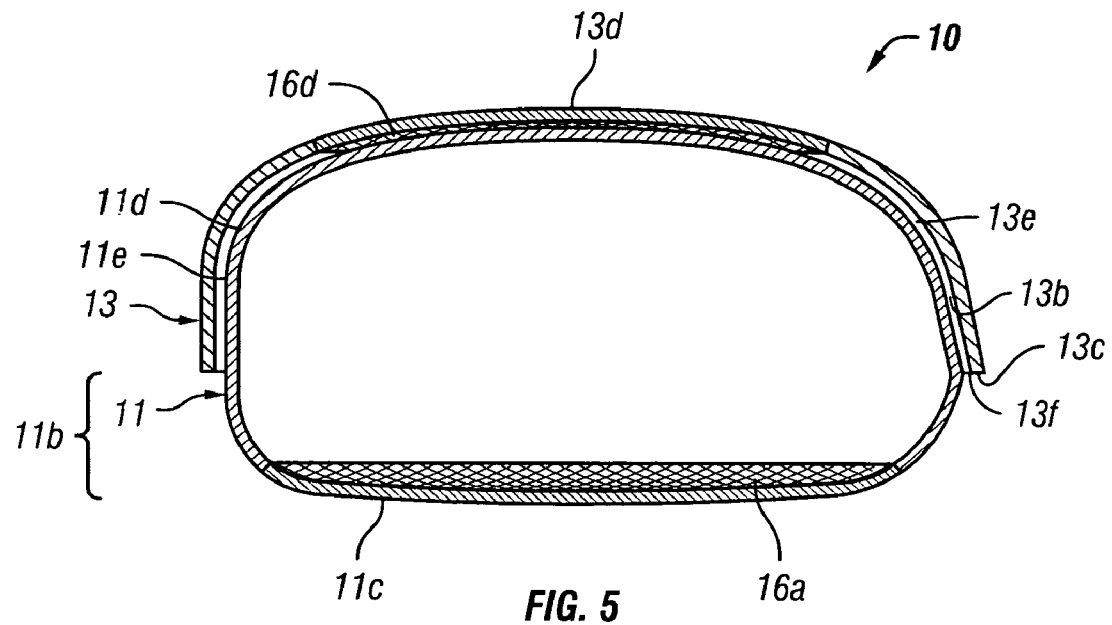
FIG. 5 is a side sectional view of the disk prosthesis of FIG. 1.

FIG. 5 shows a side sectional view of the disk prosthesis 10 as viewed from lines 5—5 of FIG. 4. FIG. 5 more clearly shows the cooperative interaction between the cap 13 and the base 11. As mentioned above, a portion 11e of the outer surface 11a of the base 11 proximate the top 11d of the base 11 cooperatively engages the inner surface 13b of the cap 13 thereby allowing at least two-degrees of freedom of movement. Motion allowed includes rotation (roll) and tilting or angulation (pitch) in any direction, but not motion in the plane from front to back or side to side (i.e., parallel to the disk space). The inner surface 13b and the portion 11e of the outer surface 11a that contacts the inner surface 13b are generally concealed.

The overall shape of the disk prosthesis 10 is designed for insertion using minimally invasive techniques through a special portal or channel allowing a replacement procedure to be implemented on an outpatient basis. The convex and contoured shape of the disk prosthesis 10 will allow the disk prosthesis 10 to be driven into an intervertebral disk space 121 by merely temporarily distracting the vertebrae with minimal removal of the vertebral rim or annulus (not shown clearly) at the point of entry, thereby reducing the chance of dislodging the device post-surgery. The smooth contour and edges of the disk prosthesis 10 provide for a safe and easy entrance into the intervertebral space 121.

The disk prosthesis 10 is a self centering device. Due largely to the shape of the disk prosthesis 10, the disk prosthesis 10 will tend to find the natural concavity of adjacent vertebrae 100. As such, placement of the disk prosthesis 10 is much faster than that of prior art intervertebral disk replacement devices, thereby effectively reducing the duration of an intervertebral disk replacement procedure and the associated risks therewith. Further, the self-centering feature of the disk prosthesis 10 will allow rapid settling of the disk prosthesis 10 into adjacent vertebral bone to promote rapid bone ingrowth while retention of most of the annulus and peripheral rim of the vertebrae 100 would provide good load sharing support to prevent excessive subsidence, where subsidence is the natural settling of intervertebral matter into a softer central portion of the vertebral bodies 106.

Figure 9:
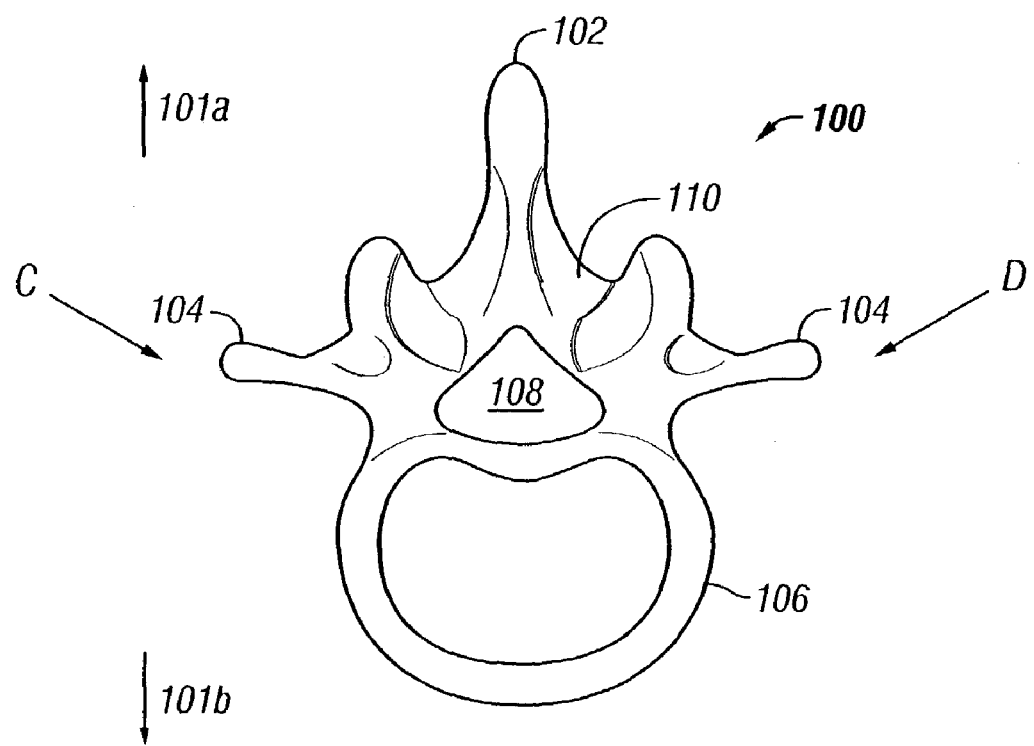
FIG. 9 is a top sectional view of a human vertebra as is known in the art.
Figure 10:
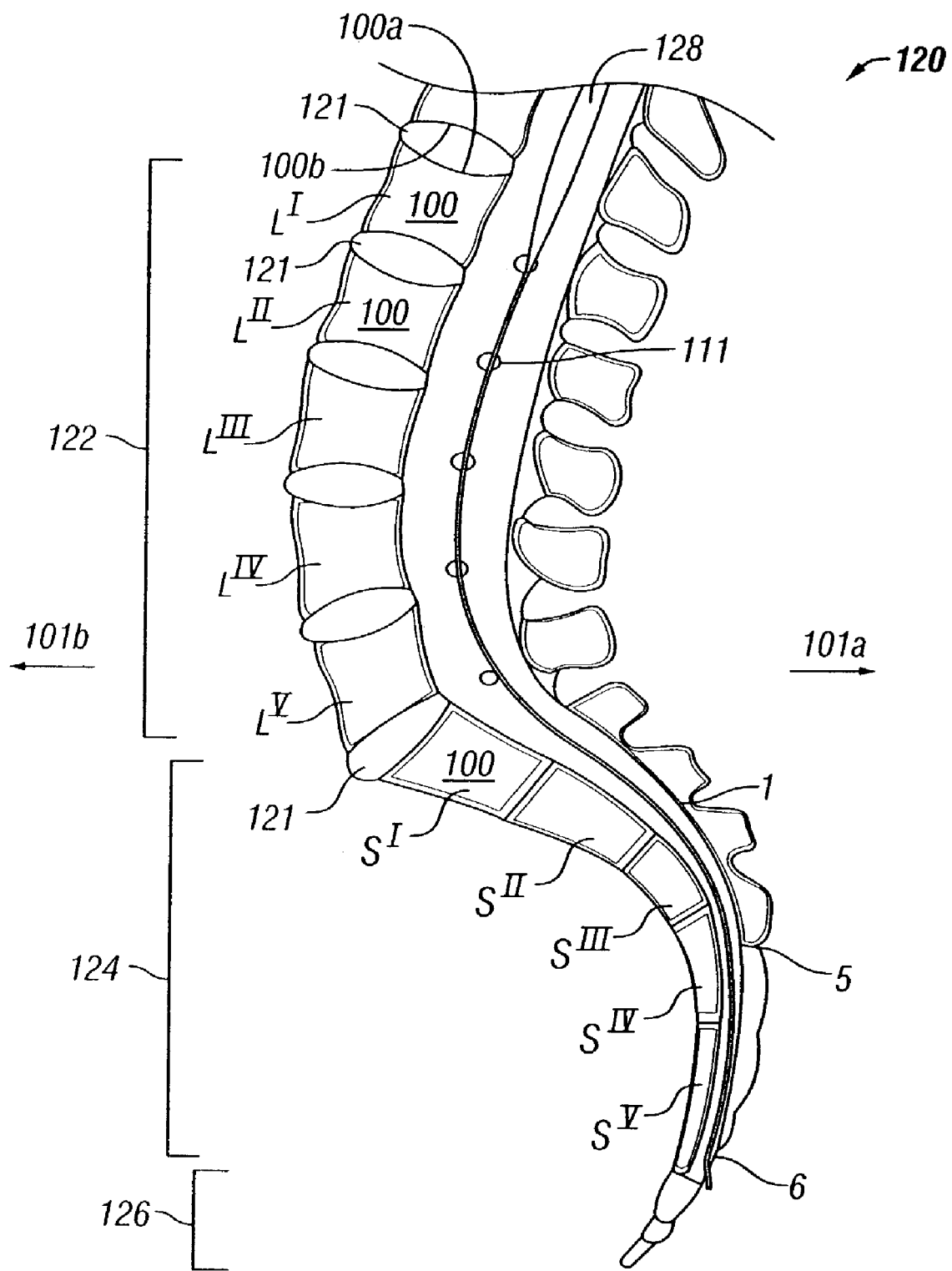
FIG. 10 is a side sectional view of a portion of a human spine as is known in the art.

FIG. 8 shows a side view of the lumbar region 122 of a portion of a human spine 120. In particular, the disk prosthesis 10 in accordance with the first preferred embodiment of the present invention is shown installed between lumbar vertebra $L^{III}$ and lumbar vertebra $L^{IV}$. In this particular installation, the second sidewall 10f of the disk prosthesis 10 is placed on the anterior side of the $L^{III}$–$L^{IV}$ intervertebral space, the first sidewall 10e of the disk prosthesis 10 is placed closest to the posterior side of the $L^{III}$–$L^{IV}$ intervertebral space, the upper wall 10d of the disk prosthesis 10 is adjacent to vertebra $L^{III}$, and the lower wall 10c of the disk prosthesis 10 is adjacent to vertebra $L^{IV}$. In this example, the surgeon would have inserted the distal end 10a of the disk prosthesis 10 into the gap between the $L^{III}$–$L^{IV}$ vertebrae as depicted in FIG. 9 by a directional arrow D. It is just as likely and possible for the surgeon to place the distal end 10a of the disk prosthesis 10 through the space between the $L^{III}$–$L^{IV}$ vertebrae in the direction of a directional arrow C (FIG. 9) or from any other direction.

Figure 6A:
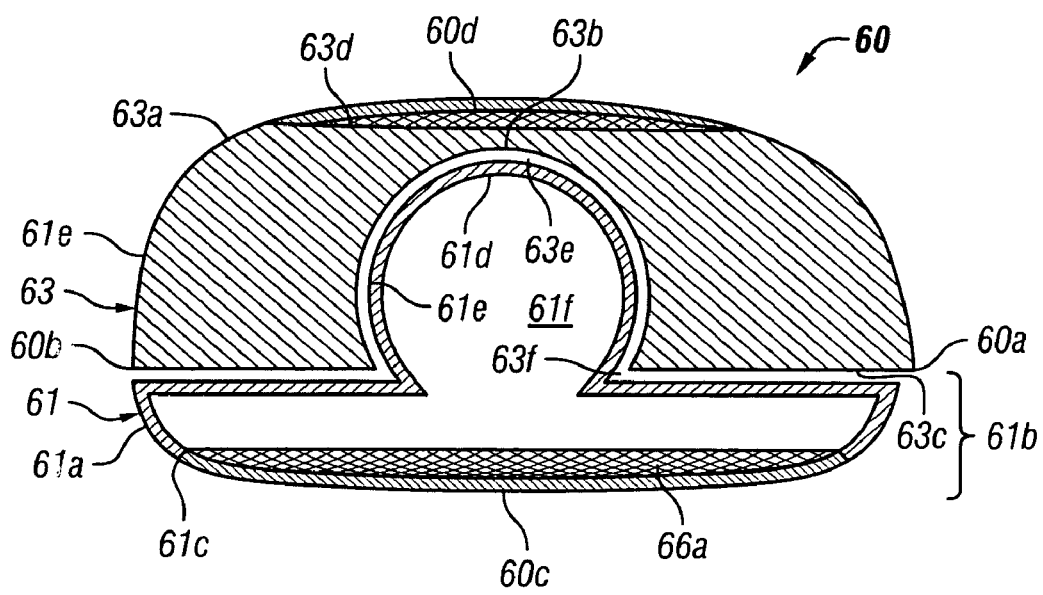
FIG. 6A is a side sectional view of a second preferred embodiment of a disk prosthesis in accordance with the present invention.

FIG. 6A shows a side sectional view of a second preferred embodiment of a disk prosthesis 60 in accordance with the present invention. The disk prosthesis 60 has a distal end 60a, a proximal end 60b, a lower wall 60c, an upper wall 60d, a first sidewall 60e (FIGS. 7A–7C), and a second sidewall (not shown). The disk prosthesis includes a first part or a cap 63. The cap 63 includes a top 63d, a bottom 63c having an opening 63f, an outer surface 63a, an inner surface 63b and a socket 63e extending into an interior of the cap 63 from the opening and defined by the inner surface 63b. The outer surface 63a proximate the top 63d contacts a concave portion 100b of a first vertebra 100. The disk prosthesis 60 further includes a second part or a base 61 including a top 61d, a bottom 61c, and an outer surface 61a. The outer surface 61a proximate the bottom 61c contacts a concave portion 100a of a second vertebra 100, and the outer surface 61a of the base 61 proximate the top 61d of the base 61 cooperatively engages the inner surface 63b of the cap 63 thereby allowing at least two-degrees of freedom of movement.

When inserted into an intervertebral space 121 the cap 63 and the base 61 function together as one overall device, i.e., the disk prosthesis 60. The cap 63 and the base 61 are preferably not mechanically connected. The base 61 is preferably not retained in the cap 63, but could be. In alternate embodiments the cap 63 and the base 61 are connected by a flexible structure or element (not shown) or are totally encased in a pliable, bio-compatible slip-cover or pouch (not shown). The inner surface 63b and a portion 61e of the outer surface 61a that contacts the inner surface 63b are preferably formed of or coated with a bio-compatible, smooth, low-friction material with high durability, such as a ceramic, an alloy or the like. The top 61d of the base 61 includes a spherically or hemispherically-shaped portion or a ball 61f. The ball 61f of the base 61 cooperatively engages the socket 63e of the cap 63 thereby mimicking a ball and socket joint such as a hip-joint. Obviously, other iterations and combinations of mutually cooperating engagement designs providing relative movement could be implemented without departing from the broad general scope of the present invention.

The lower wall 60c includes a lower mesh structure 66a and the upper wall 60d of the disk prosthesis 60 includes an upper mesh structure 66b at the point of vertebral contact to encourage successful vertebral bone ingrowth thereby affixing the cap 63 to a first or upper vertebra 100 and the base 61 to a second or lower vertebra 100 in an adjacent pair of vertebrae 100. The lower mesh 66a and the upper mesh 66b may have the attributes of the lower mesh 16a and the upper mesh 16b discussed above with reference to the first preferred embodiment.

Figure 6B:
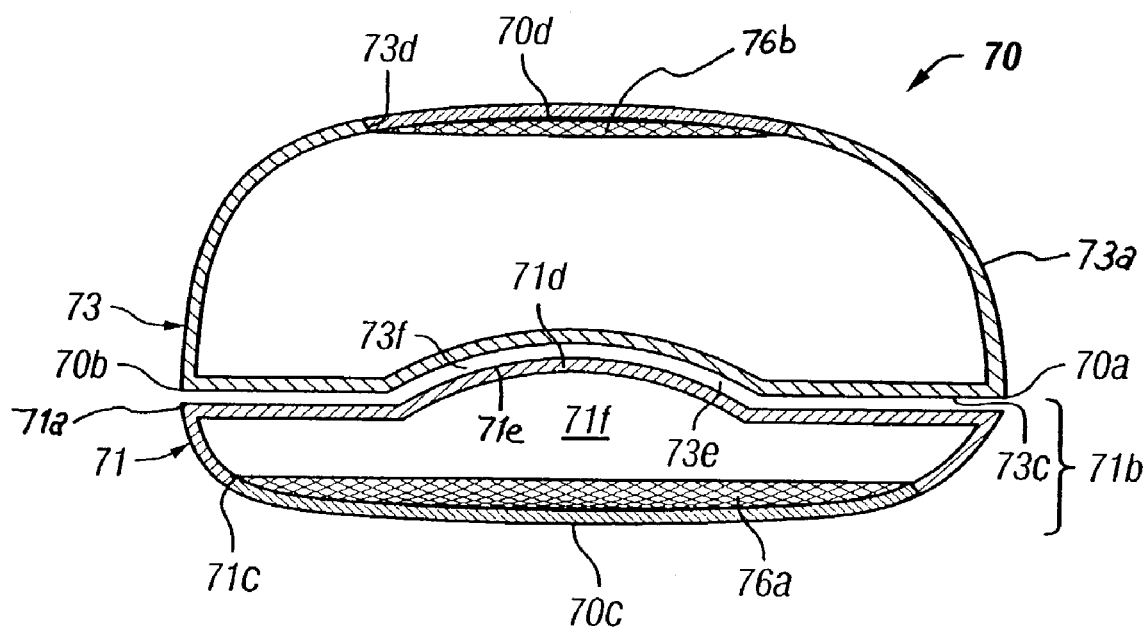
FIG. 6B is a side sectional view of a third preferred embodiment of a disk prosthesis in accordance with the present invention.

FIG. 6B shows a side sectional view of a third preferred embodiment of a disk prosthesis 70 in accordance with the present invention. The disk prosthesis 70 has a distal end 70a, a proximal end 70b, a lower wall 70c, an upper wall 70d, a first sidewall (not shown), and a second sidewall (not shown). The disk prosthesis includes a first part or a cap 73. The cap 73 includes a top 73d, a bottom 73c having an opening 73f, an outer surface 73a, an inner surface 73b and a socket 73e extending into an interior of the cap 73 from the opening and defined by the inner surface 73b. The outer surface 73a proximate the top 73d contacts a concave portion 100b of a first vertebra 100. The disk prosthesis 70 further includes a second part or a base 71 including a top 71*d*, a bottom 71*c*, and an outer surface 71*a*. The outer surface 71*a* proximate the bottom 71*c* contacts a concave portion 100*a* of a second vertebra 100, and the outer surface 71*a* of the base 71 proximate the top 71*d* of the base 71 cooperatively engages the inner surface 73*b* of the cap 73 thereby allowing at least two-degrees of freedom of movement.

When inserted into an intervertebral space 121 the cap 73 and the base 71 function together as one overall device, i.e., the disk prosthesis 70. The cap 73 and the base 71 are preferably not mechanically connected. The base 71 is preferably not retained in the cap 73, but could be. In alternate embodiments the cap 73 and the base 71 are connected by a flexible structure or element (not shown) or are totally encased in a pliable, bio-compatible slip-cover or pouch (not shown). The inner surface 73*b* and a portion 71*e* of the outer surface 71*a* that contacts the inner surface 73*b* are preferably formed of or coated with a bio-compatible, smooth, low-friction material with high durability, such as a ceramic, an alloy or the like. The top 71*d* of the base 71 includes a spherically or hemispherically-shaped portion or a ball 71*f*. The ball 71*f* of the base 71 cooperatively engages the socket 73*e* of the cap 73 thereby mimicking a ball and shallow socket joint such as a shoulder-joint. Obviously, other iterations and combinations of mutually cooperating engagement designs providing relative movement could be implemented without departing from the broad general scope of the present invention.

The lower wall 70*c* includes a lower mesh structure 76*a* and the upper wall 70*d* of the disk prosthesis 70 includes an upper mesh structure 76*b* at the point of vertebral contact to encourage successful vertebral bone ingrowth thereby affixing the cap 73 to a first or upper vertebra 100 and the base 71 to a second or lower vertebra 100 in an adjacent pair of vertebrae 100. The lower mesh 76*a* and the upper mesh 76*b* may have the attributes of the lower mesh 16*a* and the upper mesh 16*b* discussed above with reference to the first preferred embodiment.

Figure 6C:
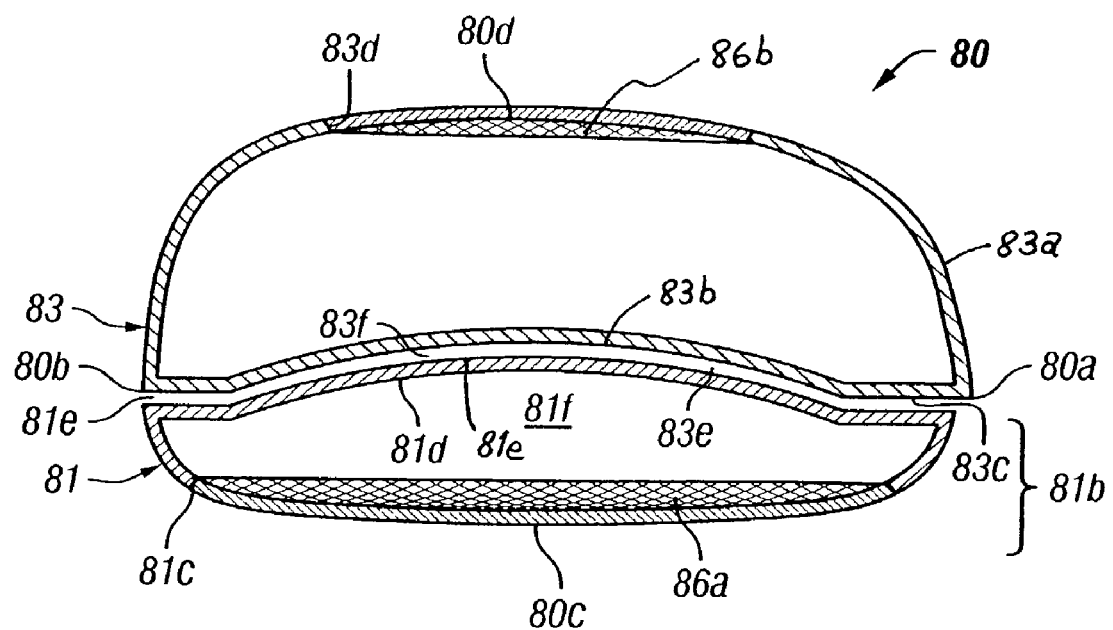
FIG. 6C is a side sectional view of a fourth preferred embodiment of a disk prosthesis in accordance with the present invention.

FIG. 6C shows a side sectional view of a fourth preferred embodiment of a disk prosthesis 80 in accordance with the present invention. The disk prosthesis 80 has a distal end 80*a*, a proximal end 80*b*, a lower wall 80*c*, an upper wall 80*d*, a first sidewall (not shown), and a second sidewall (not shown). The disk prosthesis includes a first part or a cap 83. The cap 83 includes a top 83*d*, a bottom 83*c* having an opening 83*f*, an outer surface 83*a*, an inner surface 83*b* and a socket 83*e* extending into an interior of the cap 83 from the opening and defined by the inner surface 83*b*. The outer surface 83*a* proximate the top 83*d* contacts a concave portion 100*b* of a first vertebra 100. The disk prosthesis 80 further includes a second part or a base 81 including a top 81*d*, a bottom 81*c*, and an outer surface 81*a*. The outer surface 81*a* proximate the bottom 81*c* contacts a concave portion 100*a* of a second vertebra 100, and the outer surface 81*a* of the base 81 proximate the top 81*d* of the base 81 cooperatively engages the inner surface 83*b* of the cap 83 thereby allowing at least two-degrees of freedom of movement.

When inserted into an intervertebral space 121 the cap 83 and the base 81 function together as one overall device, i.e., the disk prosthesis 80. The cap 83 and the base 81 are preferably not mechanically connected. The base 81 is preferably not retained in the cap 83, but could be. In alternate embodiments the cap 83 and the base 81 are connected by a flexible structure or element (not shown) or are totally encased in a pliable, bio-compatible slip-cover or pouch (not shown). The inner surface 83*b* and a portion 81*e* of the outer surface 81*a* that contacts the inner surface 83*b* are preferably formed of or coated with a bio-compatible, smooth, low-friction material with high durability, such as a ceramic, an alloy or the like. The top 81*d* of the base 81 includes a spherically or hemispherically-shaped portion or a ball 81*f*. The ball 81*f* of the base 81 cooperatively engages the socket 83*e* of the cap 83 thereby mimicking a ball and shallow socket joint such as a shoulder-joint. Obviously, other iterations and combinations of mutually cooperating engagement designs providing relative movement could be implemented without departing from the broad general scope of the present invention.

The lower wall 80*c* includes a lower mesh structure 86*a* and the upper wall 80*d* of the disk prosthesis 80 includes an upper mesh structure 86*b* at the point of vertebral contact to encourage successful vertebral bone ingrowth thereby affixing the cap 83 to a first or upper vertebra 100 and the base 81 to a second or lower vertebra 100 in an adjacent pair of vertebrae 100. The lower mesh 86*a* and the upper mesh 86*b* may have the attributes of the lower mesh 16*a* and the upper mesh 16*b* discussed above with reference to the first preferred embodiment.

Figure 7A:
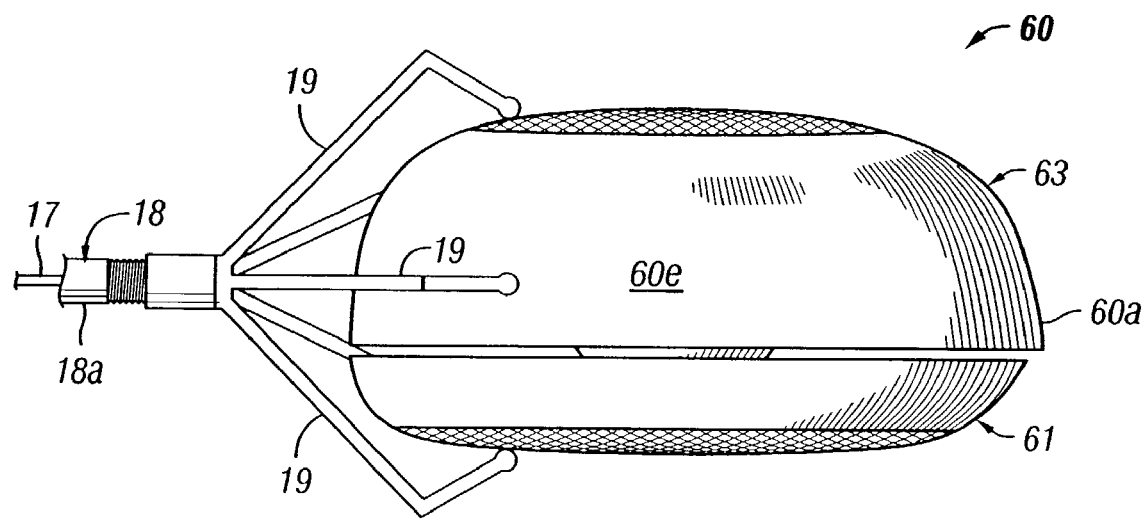
FIG. 7A is a side elevational view of the disk prosthesis of FIG. 6A connected to a first insertion tool.

FIG. 7A shows the disk prosthesis 60 of the second preferred embodiment with a specially designed first insertion tool 18 having a handle 18*a* and a plurality of resilient grasping fingers 19. The grasping fingers 19 are actuated to grasp and hold the disk prosthesis 60 by moving a tool actuation stem 17 proximally and to open and release the disk prosthesis 60 by moving the tool actuation stem 17 distally. The handle 18*a* of the first insertion tool 18 may be formed of any substantially rigid material, but preferably is formed of a material that is bio-compatible such as titanium, stainless steel, or of a bio-compatible alloy, composite, polymeric material or the like. It should be noted that the material of construction of the handle 18*a* of the first insertion tool 18 could be any material without diverging from the broad scope of the present invention. The grasping fingers 19 are preferably formed of a resilient, bio-compatible synthetic or polymeric material. It is contemplated that the grasping fingers 19 are biased by either their own resiliency or by other resilient means (not shown) such as coil springs in order to allow the grasping fingers 19 to grasp the disk prosthesis 60 without actuation but to be capable of releasing the disk prosthesis by merely twisting or moving the first insertion tool 18 proximally at a slight angle.

Figure 7B:
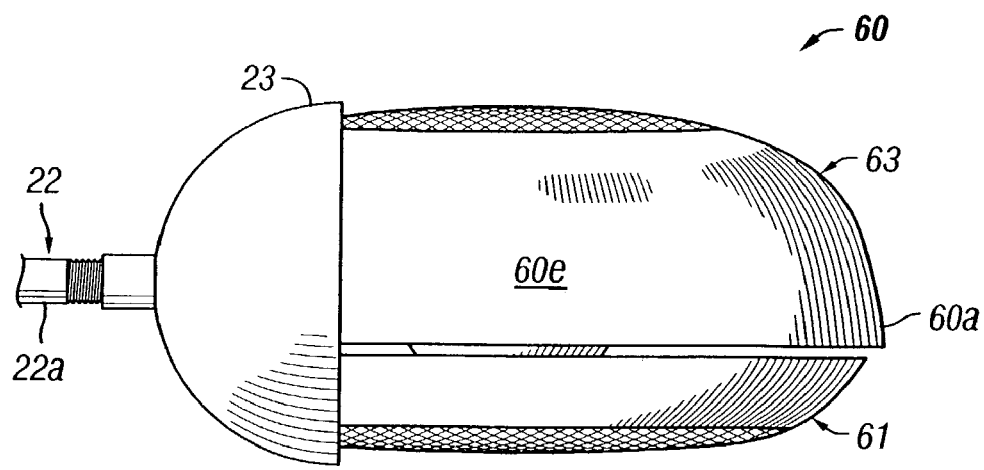
FIG. 7B is a side elevational view of the disk prosthesis of FIG. 6A connected to a second insertion tool.

FIG. 7B shows the disk prosthesis 60 of the second preferred embodiment with a specially designed second insertion tool 22 having a handle 22*a* and a suction cup 23. The handle 22*a* of the second insertion tool 22 may be formed of any substantially rigid material, but preferably is formed of a material that is bio-compatible such as titanium, stainless steel, or of a bio-compatible alloy, composite, polymeric material or the like. It should be noted that the material of construction of the handle 22*a* of the second insertion tool 22 could be any material without diverging from the broad scope of the present invention. The suction cup 23 is preferably formed of a resilient, bio-compatible synthetic or polymeric material. Preferably, the suction cup 23 is biased inwardly by its own resiliency in order to allow the suction cup 23 to grasp the disk prosthesis 60 without actuation but to be capable of releasing the disk prosthesis by merely twisting or moving the second insertion tool 22 proximally at a slight angle.

Figure 7C:
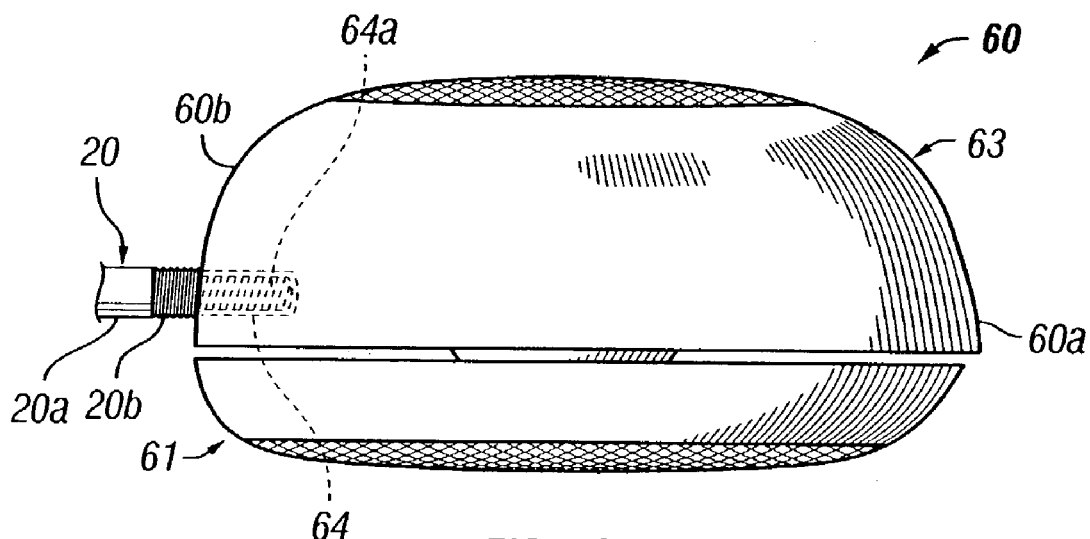
FIG. 7C is a side elevational view of the disk prosthesis of FIG. 6A connected to a third insertion tool.

FIG. 7C shows the disk prosthesis 60 of the second preferred embodiment with a specially designed third insertion tool 20 having a handle 20*a* and being threaded into a socket 64 with female threads 64*a* by male threads 20*b* of the third insertion tool 20. The handle 20a of the third insertion tool 20 may be formed of any substantially rigid material, but preferably is formed of a material that is bio-compatible such as titanium, stainless steel, or of a bio-compatible alloy, composite, polymeric material or the like. It should be noted that the material of construction of the third insertion tool 20 could be any material without diverging from the broad scope of the present invention. Design of insertion tools are not critical to the present invention, and a variety of tool designs are contemplated for use with various disk prostheses.

Figure 11A:
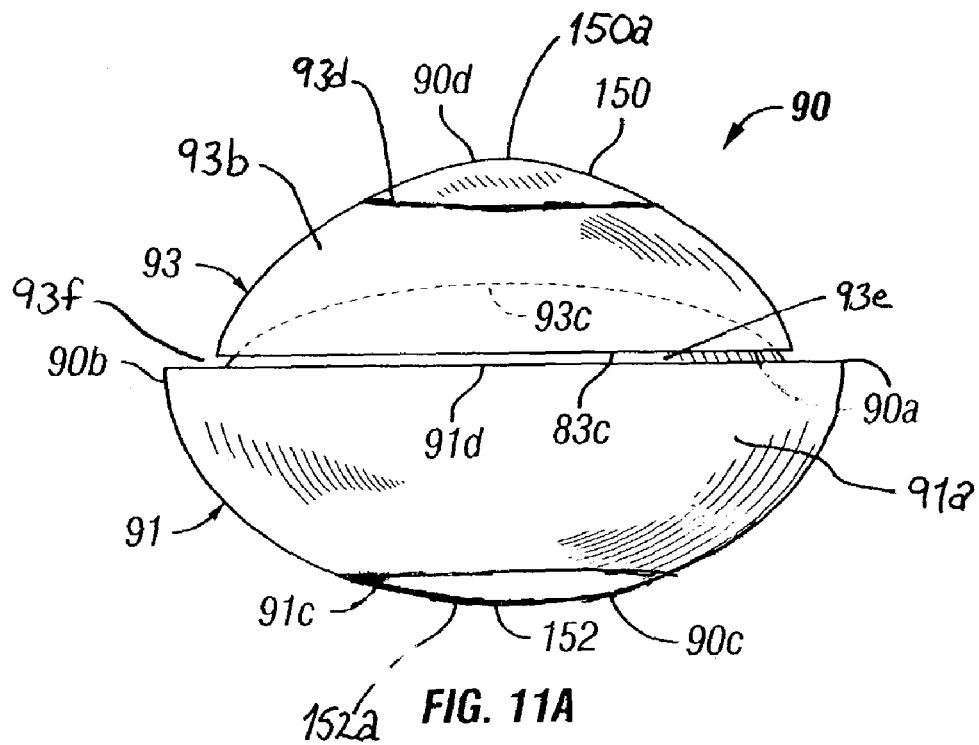
FIG. 11A is a side elevational view of a fifth preferred embodiment of a disk prosthesis in accordance with the present invention.
Figure 11B:
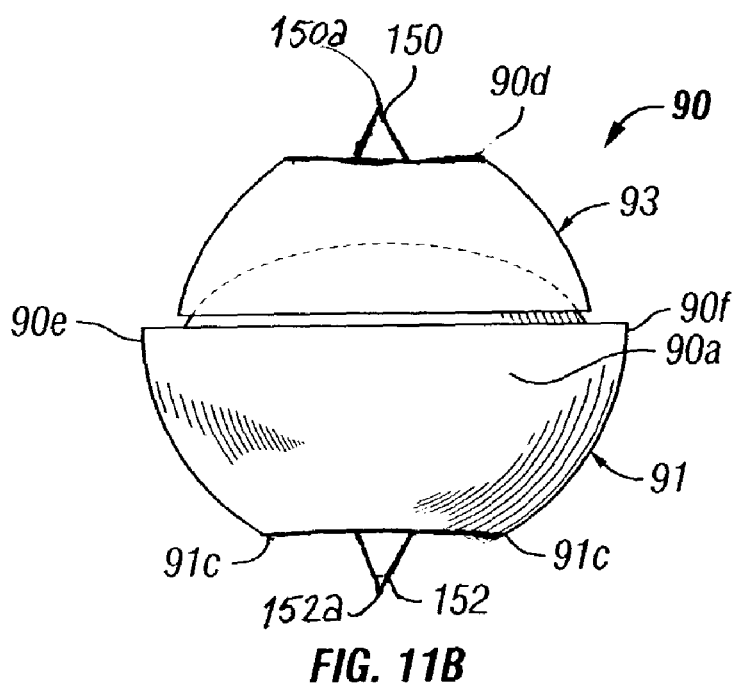
FIG. 11B is a front elevational view of the disk prosthesis of FIG. 11A.

FIGS. 11A–11B show a fifth preferred embodiment of a disk prosthesis in accordance with the present invention. The disk prosthesis 90 has a distal end 90a, a proximal end 90b, a lower wall 90c, an upper wall 90d, a first sidewall (not shown), and a second sidewall (not shown). The disk prosthesis includes a first part or a cap 93. The cap 93 includes a top 93d, a bottom 93c having an opening 93f, an outer surface 93a, an inner surface 93b and a socket 93e extending into an interior of the cap 93 from the opening and defined by the inner surface 93b. The outer surface 93a proximate the top 93d contacts a concave portion 100b of a first vertebra 100. The disk prosthesis 90 further includes a second part or a base 91 including a top 91d, a bottom 91c, and an outer surface 91a. The outer surface 91a proximate the bottom 91c contacts a concave portion 100a of a second vertebra 100, and the outer surface 91a of the base 91 proximate the top 91d of the base 91 cooperatively engages the inner surface 93b of the cap 93 thereby allowing at least two-degrees of freedom of movement. The cap 93 is preferably slightly smaller than the base 91 in both length and width in order to allow freedom movement even when bone growth reaches near the edges of the cap 93 and/or base 91. Alternatively, the base 91 may be slightly smaller than the cap 93 for similar reasons without departing from the present invention.

Further, the disk prosthesis 90 includes at least one upper arch 150 and at least one lower arch 152, but preferably the disk prosthesis 90 includes three upper arches 150 and three lower arches 152. The arches 150, 152 are generally disposed symmetrically along and about a centerline of the longer axis of the disk prosthesis 90 and are secured to the body of the disk prosthesis 90. Of course the arches 150, 152 may be secured to the disk prosthesis 90 by other means and may be disposed in other orientations without departing from the spirit of the present invention. Preferably, the arches 150, 152 protrude above the top and bottom 190d, 190c of the disk prosthesis 90, respectively. The arches 150, 152 are configured to settle into bone matter, and therefore, the arches 150, 152 have sharpened edges 150a, 152a. The sharpened edges 150a, 152a may include serrations, pins, sharpened cones or a simple knife-like edge, but need not be. Preferably, the sharpened edges 150a, 152a are partially knife like proximate the ends of the arches and partially covered with sharpened cones 153. The arches 150, 152 are preferably about 0.5 mm to about 2.0 mm wide. The arches 150, 152 also serve to center the disk prosthesis 90 during placement and prevent the disk prosthesis 90 from rolling or canting thereafter.

Figure 12A:
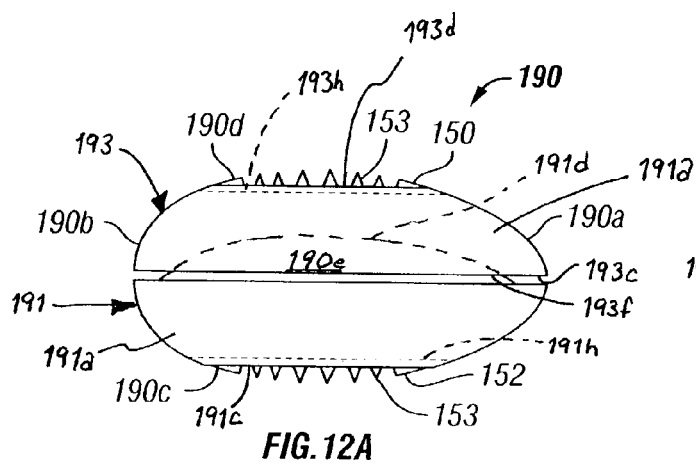
FIG. 12A is a side elevational view of a sixth preferred embodiment of a disk prosthesis in accordance with the present invention.
Figure 12B:
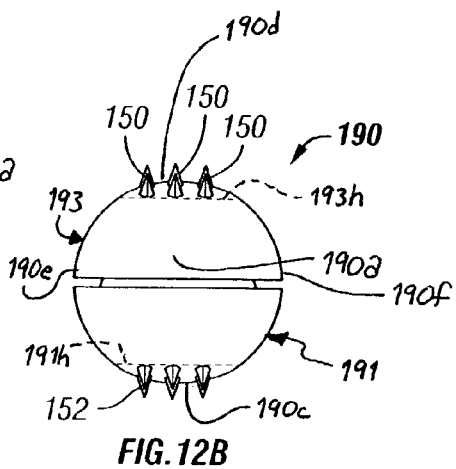
FIG. 12B is a front elevational view of the disk prosthesis of FIG. 12A.

FIGS. 12A–12B show a sixth preferred embodiment of a disk prosthesis 190 in accordance with the present invention. The disk prosthesis 190 has a distal end 190a, a proximal end 190b, a lower wall 190c, an upper wall 190d, a first sidewall 190e, and a second sidewall 190f. The disk prosthesis includes a first part or a cap 193. The cap 193 includes a top 193d, a bottom 193c having an opening 193f, an outer surface 193a, an inner surface (not shown) and a socket (not shown) extending into an interior of the cap 193 from the opening and defined by the inner surface. The outer surface 193a proximate the top 193d contacts a concave portion 100b of a first vertebra 100. The disk prosthesis 190 further includes a second part or a base 191 including a top 191d, a bottom 191c, and an outer surface 191a. The outer surface 191a proximate the bottom 191c contacts a concave portion 100a of a second vertebra 100, and the outer surface 191a of the base 191 proximate the top 191d of the base 191 cooperatively engages the inner surface (not shown) of the cap 193 thereby allowing at least two-degrees of freedom of movement. Further, the disk prosthesis 190 includes at least one upper arch 150 and at least one lower arch 152, but preferably the disk prosthesis 190 includes three upper arches 150 and three lower arches 152 similar to the disk prosthesis 90. The arches 150, 152 are generally disposed symmetrically along and about a centerline of the longer axis of the disk prosthesis 190 and are secured to the body of the disk prosthesis 190. The top of the cap 193 has a recess and the bottom of the base 191 has a recess, the recesses include a platform 193h and 191h, respectively. The platforms 191h, 193h are preferably are texturized and/or coated with a material to promote bone growth.

Figure 13A:
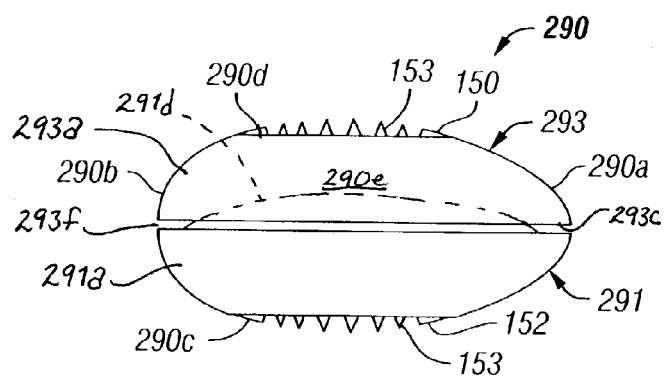
FIG. 13A is a side elevational view of a seventh preferred embodiment of a disk prosthesis in accordance with the present invention.
Figure 13B:
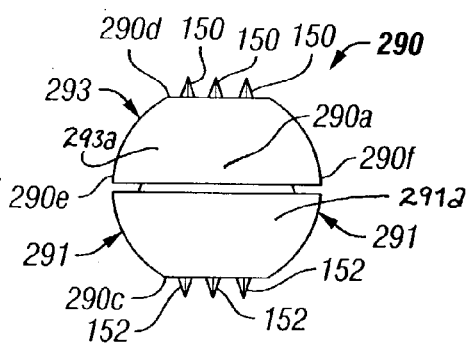
FIG. 13B is a front elevational view of the disk prosthesis of FIG. 13A.

FIGS. 13A–13B show a seventh preferred embodiment of a disk prosthesis 290 in accordance with the present invention. The disk prosthesis 290 has a distal end 290a, a proximal end 290b, a lower wall 290c, an upper wall 290d, a first sidewall 290e, and a second sidewall 290f. The disk prosthesis includes a first part or a cap 293. The cap 293 includes a top 293d, a bottom 293c having an opening 293f, an outer surface 293a, an inner surface (not shown) and a socket (not shown) extending into an interior of the cap 293 from the opening and defined by the inner surface. The outer surface 293a proximate the top 293d contacts a concave portion 100b of a first vertebra 100. The disk prosthesis 290 further includes a second part or a base 291 including a top 291d, a bottom 291c, and an outer surface 291a. The outer surface 291a proximate the bottom 291c contacts a concave portion 100a of a second vertebra 100, and the outer surface 291a of the base 291 proximate the top 291d of the base 291 cooperatively engages the inner surface (not shown) of the cap 293 thereby allowing at least two-degrees of freedom of movement. Further, the disk prosthesis 290 includes at least one upper arch 150 and at least one lower arch 152, but preferably the disk prosthesis 290 includes three upper arches 150 and three lower arches 152 similar to the disk prosthesis 90. The arches 150, 152 are generally disposed symmetrically along and about a centerline of the longer axis of the disk prosthesis 290 and are secured to the body of the disk prosthesis 290. The top of the cap 293 and the bottom of the base 291 are preferably flatly shaped. The flat surfaces preferably are texturized and/or coated with a material to promote bone growth.

Figure 14A:
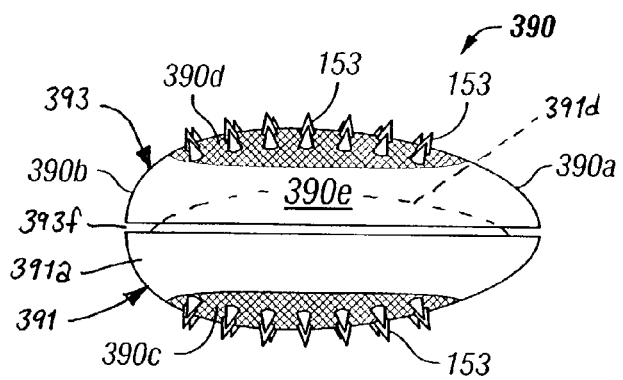
FIG. 14A is a side elevational view of an eighth preferred embodiment of a disk prosthesis in accordance with the present invention.
Figure 14B:
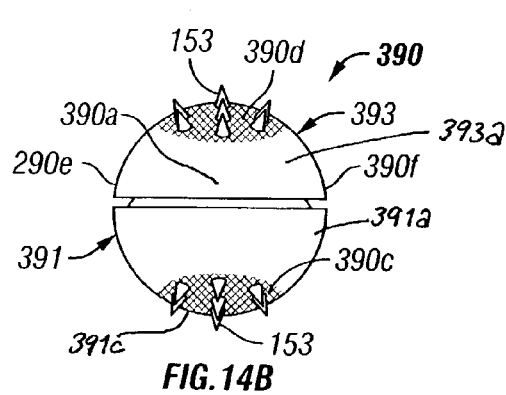
FIG. 14B is a front elevational view of the disk prosthesis of FIG. 14A.

FIGS. 14A–14B show an eighth preferred embodiment of a disk prosthesis 390 in accordance with the present invention. The disk prosthesis 390 has a distal end 390a, a proximal end 390b, a lower wall 390c, an upper wall 390d, a first sidewall 390e, and a second sidewall 390f. The disk prosthesis includes a first part or a cap 393. The cap 393 includes a top 393d, a bottom 393c, an outer surface 393a, an inner surface (not shown) and a socket (not shown) extending into an interior of the cap 393 from the opening and defined by the inner surface 393b. The outer surface 393a proximate the top 393d contacts a concave portion 100b of a first vertebra 100. The disk prosthesis 390 further includes a second part or a base 391 including a top 391d, a bottom 391c, and an outer surface 391a. The outer surface 391a proximate the bottom 391c contacts a concave portion 100a of a second vertebra 100, and the outer surface 391a of the base 391 proximate the top 391d of the base 391 cooperatively engages the inner surface (not shown) of the cap 393 thereby allowing at least two-degrees of freedom of movement. Further, the disk prosthesis 390 includes at least one row of sharpened cones 153 on the top of the cap 393 and at least one row of sharpened cones 153 on the bottom of the base 391, but preferably the disk prosthesis 390 includes three rows of sharpened cones 153 on the top of the cap 393 and three rows of sharpened cones 153 on the bottom of the base 391. The rows of sharpened cones 153 are generally disposed symmetrically along and about a centerline of the longer axis of the disk prosthesis 390 and are secured to the body of the disk prosthesis 390. The top of the cap 393 and the bottom of the base 391 are preferably convexly shaped to more readily find the contours of the concave portions 100a, 100b of adjacent vertebrae 100. Preferably, the surface of the disk prosthesis 390 proximate the rows of sharpened cones 153 is texturized and/or coated with a material to promote bone growth such as hydroxyapatite.

Figure 15A:
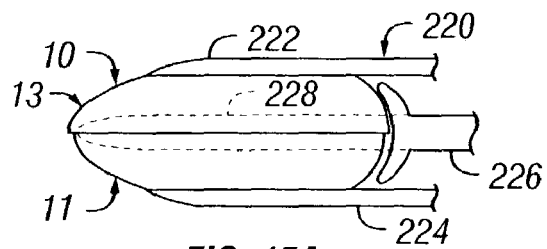
FIG. 15A is a side elevational view of a fourth insertion tool for a disk prosthesis in accordance with the present invention.
Figure 15B:
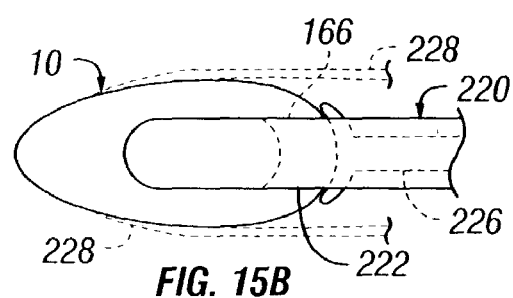
FIG. 15B is a top plan view of the insertion tool of FIG. 15A.

FIGS. 15A–15B show a fourth insertion tool 220 for a disk prosthesis 10 (60, 70, or 80) having lower and upper openings 16a, 16b (66a, 66b, 76a, 76b, 86a, 86b), respectively. The insertion tool 220 has a first finger 224 configured to cooperatively engage the lower opening 16a and a second finger 222 configured to cooperatively engage the upper opening 16b. The fingers 222, 224 have outer surfaces which are shaped to match the contoured shape of the disk prosthesis 10 to allow a smooth insertion of the disk prosthesis 10. The combination of the insertion tool 220 and the disk prosthesis 10 when the first and second fingers 222, 224 are engaged with the ingrowth openings 16a, 16b, forms a combined structure having generally rounded exposed surfaces. The fingers 222, 224 also prevent foreign matter and debris from getting caught in the openings 16a, 16b during insertion. Because the fingers 222, 224 grasp the disk prosthesis 10 in a specific orientation defined by the upper and lower openings 16a, 16b, the insertion tool 220 provides the surgeon with means to orient the disk prosthesis 10 correctly during insertion.

The insertion tool 220 further includes a driving member 226 that is configured to engage the body of the disk prosthesis 10. The driving member 226 is configured to be impacted such that during insertion a surgeon may tap or hammer the driving member 226 to push the disk prosthesis 10 through a small opening. Preferably, the first and second fingers 222, 224 are retractable relative to the driving member 226. Thus, after the disk prosthesis 10 is inserted to a desired position, the first and second fingers 222, 224 are retracted while the driving member 226 holds the disk prosthesis 10 in place. Optionally, the disk prosthesis 10 may have grooves 166 (shown in phantom in FIG. 15B) extending from the upper and lower openings 16a, 16b to facilitate the removal of the retractable fingers 222, 224. Optionally, the insertion tool 220 includes third and fourth fingers 228 (shown in phantom in FIGS. 15A–15B) configured to retractably move along the space between the upper part 13 and the lower part 11 of the body of the disk prosthesis 10.

Figure 16A:
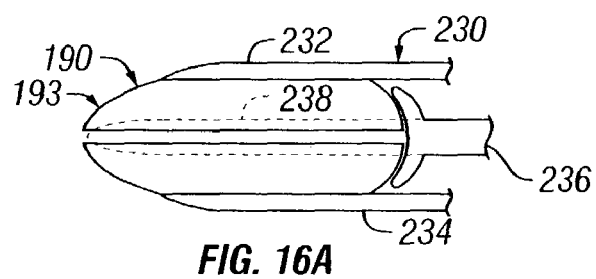
FIG. 16A is a side elevational view of a fifth insertion tool for a disk prosthesis in accordance with the present invention.
Figure 16B:
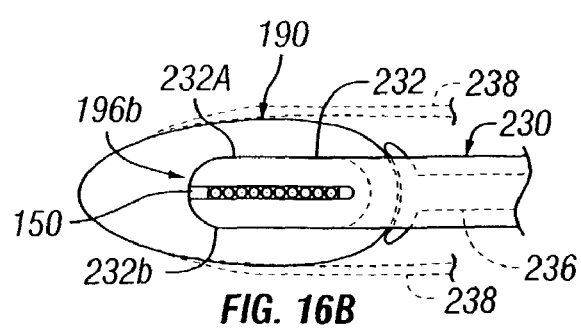
FIG. 16B is a top plan view of the insertion tool of FIG. 16A.

FIGS. 16A–16B is a side elevational view of a fifth insertion tool 230 for a disk prosthesis 90 (190, 290 or 390) having upper and lower openings 96a, 96b and upper and lower arches 150, 152. For example, the upper finger 232 has first and second prongs 232a, 232b for straddling the upper arches 150 as best seen in FIG. 16B. The insertion tool 230 is similar to the insertion tool 220, but each of the retractable fingers 232, 234 is forked to accommodate the arches 150, 152. Preferably, the arches 150, 152 and the rows of cones 153 are just below the outer surface of the fingers 232, 234, so that the arches 150, 152 do not injure adjacent tissue during insertion. Optionally, the insertion tool 230 includes third and fourth fingers 238 (shown in phantom in FIGS. 16A–16B) configured to retractably move between the space between the upper part 93 and the lower part 91 of the body of the disk prosthesis 90. Furthermore, it would be obvious to one skilled in the art to utilize multiple prongs in each of the retractable fingers 232, 234 in order to accommodate multiple arches 150, 152 (such as on disk prostheses 190 and 290) and multiple rows of sharpened cones 153 (such as on disk prosthesis 390).

Preferably, the intervertebral disk prostheses 10, 60, 70, 90, 190, 290 and 390 have a freedom of movement that is limited to between about 2–15 degrees tilt in any direction. The annular ligament of a human being is built for physiologic limiting thereby stopping over rotation. The facets in the lumbar region also limit rotation and tilt.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An intervertebral disk prosthesis having a convexly tapered distal end, a convexly tapered proximal end, an anterior side and a posterior side, the intervertebral disk prosthesis further comprising:
  an upper part including a convexly-shaped and rounded top, a bottom having an opening, an outer surface, an inner surface and a socket extending into an interior of the upper part from the opening, the outer surface proximate the top being configured to contact a concave portion of a first vertebra; and
  a lower part including a top, a convexly-shaped and rounded bottom, and an outer surface, the outer surface proximate the bottom being configured to contact a concave portion of a second vertebra that is adjacent to the first vertebra, and the outer surface of the lower part proximate the top of the lower pan being cooperatively and movably overlapped by the inner surface of the upper part thereby allowing at least two-degrees of freedom of movement,
  the taper of the distal end diminishing more gradually than the taper of the proximal end, and
  the anterior and posterior sides are at least partially convexly shaped in order to allow installation of the intervertebral disk prosthesis into a space defined by the concavities of the adjacent first and second vertebrae.

2. The intervertebral disk prosthesis of claim 1, wherein the top of the upper part has an ingrowth opening to encourage vertebral ingrowth and is configured to align the intervertebral disk prosthesis within an intervertebral space.

3. The intervertebral disk prosthesis of claim 2, further comprising a generally continuous sheet of biocompatible porous material at least partially spanning the ingrowth opening.

4. The intervertebral disk prosthesis of claim 3, wherein the porous material is hydroxyapatite-coated metal.

5. The intervertebral disk prosthesis of claim 2, further comprising a mesh structure at least partially spanning the ingrowth surface.

6. The intervertebral disk prosthesis of claim 1, wherein the bottom of the lower part has an ingrowth opening to encourage vertebral ingrowth and is configured to align the intervertebral disk prosthesis within an intervertebral space.

7. The intervertebral disk prosthesis of claim 6, further comprising a generally continuous sheet of biocompatible porous material at least partially spanning the ingrowth surface.

8. The intervertebral disk prosthesis of claim 7, wherein the porous material is hydroxyapatite-coated metal.

9. The intervertebral disk prosthesis of claim 6, further comprising a mesh structure at least partially spanning the ingrowth surface.

10. The intervertebral disk prosthesis of claim 1, wherein the distal end of the intervertebral prosthesis is generally bluntly rounded.

11. The intervertebral disk prosthesis of claim 1, wherein the proximal end of the intervertebral prosthesis is generally bluntly rounded.

12. The intervertebral disk prosthesis of claim 1, wherein an exterior surface of the intervertebral prosthesis is generally rounded.

13. The intervertebral disk prosthesis of claim 1, wherein the intervertebral prosthesis is formed at least partially of a biocompatible material selected from the group consisting of stainless steel, titanium, cobalt-chrome alloy, nickel plated metal, a biocompatible alloy, a biocompatible ceramic, and a biocompatible polymeric material.

14. The intervertebral disk prosthesis of claim 1, further comprising a pliable, biocompatible slip-cover that covers at least a portion of the upper part and a portion of the lower part, the slip-cover being configured to flexibly retain the movably coupled upper and lower parts.

15. The intervertebral disk prosthesis of claim 1, wherein the length of the intervertebral prosthesis as measured from the distal end to the proximal end is between about 10 mm and about 30 mm.

16. The intervertebral disk prosthesis of claim 1, wherein the width of the intervertebral prosthesis as measured between the anterior side and the posterior side is between about 10 mm and about 25 mm.

17. The intervertebral disk prosthesis of claim 1, wherein the height of the intervertebral prosthesis as measured between the top of the upper part and the bottom of the lower part is between about 5 mm and about 25 mm.

18. The intervertebral disk prosthesis of claim 1, wherein the freedom of movement is limited to between about 2–15 degrees tilt in any direction.

19. The intervertebral disk prosthesis of claim 1, wherein the disk prosthesis minimizes translational movement.

20. An intervertebral disk prosthesis having a convexly tapered distal end, a convexly tapered proximal end, anterior side and a posterior side, the intervertebral disk prosthesis further comprising:

a lower part including a convexly-shaped and rounded bottom, a top having an opening, an outer surface, an inner surface and a socket extending into an interior of the lower part from the opening, the outer surface proximate the bottom being configured to contact a concave portion of a first vertebra; and an upper part including a bottom, a convexly-shaped and rounded top, and an outer surface, the outer surface proximate the top being configured to contact a concave portion of a second vertebra that is adjacent to the first vertebra, and the outer surface of the lower part proximate the bottom of the upper part being cooperatively and movably overlapped by the inner surface of the upper part thereby allowing at least two-degrees of freedom of movement, the taper of the distal end diminishing more gradually than the taper of the proximal end, and the anterior and posterior sides are at least partially convexly shaped in order to allow installation of the intervertebral disk prosthesis into a space defined by the concavities of the adjacent first and second vertebrae.

* * * * *

UNITED STATES PATENT AND TRADEMARK OFFICE
CERTIFICATE OF CORRECTION

PATENT NO. : 7,011,684 B2  Page 1 of 1
APPLICATION NO. : 10/345634
DATED : March 14, 2006
INVENTOR(S) : Walter W. Eckman It is certified that error appears in the above-identified patent and that said Letters Patent is hereby corrected as shown below:

Column 14, line 46, "pan" should read -- part --.

Signed and Sealed this

Twelfth Day of August, 2008

JON W. DUDAS
*Director of the United States Patent and Trademark Office*